United States Patent [19]

Renvall et al.

[11] 4,008,256
[45] Feb. 15, 1977

[54] ESTERIFICATION OF FURFURYL ALCOHOL AND ITS DERIVATES

[75] Inventors: Ilkka Renvall, Suomenoja; Tapio Mattila, Kivenlahti, both of Finland

[73] Assignee: Kemira Oy, Finland

[22] Filed: Aug. 7, 1975

[21] Appl. No.: 602,550

[30] Foreign Application Priority Data

Aug. 15, 1974 Finland .................................. 2424/74

[52] U.S. Cl. ............................................. 260/347.4
[51] Int. Cl.² ........................................ C07D 307/46
[58] Field of Search ................................ 260/347.4

[56] References Cited

UNITED STATES PATENTS

| 2,769,744 | 11/1956 | Usteri | 260/347.4 |
| 2,847,424 | 8/1958 | Ward | 260/347.4 |
| 2,944,059 | 7/1960 | Elming | 260/347.4 |
| 3,465,007 | 9/1969 | Elliott | 260/347.4 |
| 3,567,740 | 3/1971 | Matsui et al. | 260/347.4 |
| 3,573,328 | 3/1971 | Nakanishi et al. | 260/347.4 |
| 3,600,407 | 8/1971 | Levin et al. | 260/347.4 |
| 3,629,269 | 12/1971 | Karmas | 260/347.4 |
| 3,669,989 | 10/1972 | Itaya et al. | 260/347.4 |
| 3,843,690 | 10/1974 | Katsuda | 260/347.4 |

*Primary Examiner*—Natalie Trousof
*Assistant Examiner*—Bernard Dentz
*Attorney, Agent, or Firm*—Bucknam and Archer

[57] ABSTRACT

Furfuryl alcohol is esterified by means of an aliphatic anhydride or its halogen derivative using aliphatic, tertiary amines as catalysts.

7 Claims, No Drawings

ESTERIFICATION OF FURFURYL ALCOHOL AND ITS DERIVATES

BACKGROUND OF THE INVENTION

The invention relates to the esterification of furfuryl alcohol and its derivates by means of aliphatic acid anhydrides, with aliphatic tertiary amines as catalysts. According to the invention the compounds obtained by the method can as such be used as biologically active substances against, for example, molds, fungi or bacteria or as intermediates in the production of such slimecides. These compounds can also be used as fragrancies.

It is generally known that ordinary alcohols can be normally esterified with acid anhydrides, using acids or bases as catalysts. It is also known that furfuryl alcohol and several substituted furfuryl alcohols decompose and polymerize under acid conditions. For this reason the esterification of such substances cannot be normally performed by acid catalysis, using mineral acids, e.g., sulfuric acid, as a catalyst and the organic acid in question for the esterification. It is known, for example, that furfuryl alcohol can be esterified with acetic anhydride. [J. E. Zanetti, J. Amer. Chem. Soc. 47 (19250 pp. 535-536]. The synthesis is performed by heating furfuryl alcohol and various acid anhydrides at 130°–150° C for 2 hours. Yields are not mentioned. The normal method for preparing furfuryl alcohol ester of acetic acid is, however, to use acetic anhydride as the condensing agent and water-free (smelted) sodium acetate as an auxiliary condensing agent (Org. Synth. Coll. Vol. 2nd ed., John Wiley & Son, Inc., New York 1967, pp. 285-286). The synthesis is performed by using benzene as the medium and the reflux temperature of benzene as the reaction temperature. After the reaction the mixture is poured into water, it is neutralized with sodium bicarbonate solution, the benzene solution is washed with water, and the benzene is distilled off. Thereafter the product is distilled. The drawbacks of the method are the great need for water-free sodium acetate, the neutralization of the mixture after the reaction, the distillation off of the auxiliary agent benzene and in addition, a yield of only 87–93%, consisting of a product with a concentration of 93–94%.

Poorly water soluble derivates of furfuryl alcohol, such as 5-nitro-2-furfuryl alcohol, can also be esterified by acid catalysis by means of, for example, sulfuric acid (M. Ja. Buklava et al., Latvijas PSR Zinatnu Akad. Vestis, Kim. ser. (1963):3, pp. 349-355). The drawback of this method is that, for example, isopropanol must be used as the medium and the yields are usually approx. 80%. The method is not applicable to, for example, furfuryl alcohol.

SUMMARY OF THE INVENTION

It has now unexpectedly been observed that furfuryl alcohol and some of its derivates can be esterified with a good yield on an industrial scale by means of acid anhydrides, using aliphatic tertiary amines as a catalyst. They can be tertiary amines with the formula

such as trimethyl, triethyl, tributyl, tri-isobutyl amine. The practicable mole ratio is $\geq$ 1 mole acid anhydride and $\leq$ 0.05 mole tertiary amine per 1 mole furfuryl alcohol, preferably 1–1.2 mole acid anhydride and 0.05–0.5 mole tertiary amine. Larger quantities of acid anhydride can be used but no special advantage is thereby achieved. The reaction temperature can be varied within a wide range, e.g., 0°–100° C and preferably 15°–80° C. The reaction can also be performed at a temperature above 100° C, but this has not been observed to have any practical effect on the yields. For this reason it is advantageous to perform the reactions so that the reaction mixture is heated by the heat of reaction. The reaction times vary mainly depending on the used mole ratios so that longer reaction times are required when using small catalyst quantities than when using larger catalyst quantities. However, large catalyst quantities, in many cases >0.5 mole/furfuryl alcohol or its derivate do not substantially accelerate the reaction but only increase the manufacturing expenses if the catalyst is not recovered. The method according to the invention has an advantage in that the reactions proceed within a very wide temperature range. Also, no medium is required in the reactions. Several esters can be manufactured with a yield of almost 100% by the method according to the invention. The total reaction is as follows:

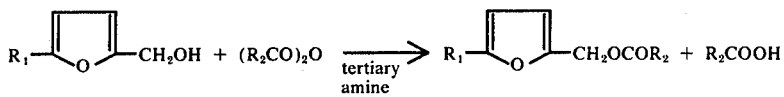

The method also has an advantage in that the catalysts can be recovered from the washing water, which for its part reduces the waste water load. When water-soluble amines, e.g., triethyl amine, are concerned, the amine can be recovered in a normal manner, e.g., by distillation. When using relatively water-insoluble amines as the catalyst, such as tributyl amine, we have observed that the amine can be easily recovered from the washing water by neutralizing the washing water and by decanting the amine from the water solution. Thus $\geq$ 90% of the amine can be recovered easily and inexpensively, which considerably improves the usefulness of the method by lowering the manufacturing cost and reducing the waste water problems. When a relatively poorly water-soluble amine is applied some acid can be used advantageously in the wash to improve the phase separation in the wash by improving the settling. In the equation hereinabove $R_2$ may be an alkyl substituted with a halogen atom.

EXAMPLE 1

5.06 g triethyl amine (0.05 mole) was added to 112.3 g (1.10 mole) acetic anhydride. 98.1 g (1.00 mole) distilled furfuryl alcohol was added thereafter at 15°–22° C in the course of 25 minutes. The mixture was stirred for 24 hours at room temperature. After the reaction the mixture weighed 214.5 g and it contained 64.1% furfuryl acetate, i.e., the yield was 98.1%. The product was washed 3 times with 200 ml water. Furfuryl acetate was taken from the bottom of the reactor in a quantity of 139.5 g. The concentration of furfuryl acetate in this product was 91.3%, i.e., the yield was 90.9%.

EXAMPLE 2

A mixture of 490.5 g technical furfuryl alcohol (concentration 96.7% = 4.835 mole) and 101.2 g (1.00 mole) triethyl amine was added to 561.2 g (5.50 mole) acetic anhydride in the course of 15 minutes. During the addition the temperature rose to 48.5° C. After the addition the mixture was stirred without heating for 5.5 hours, whereby the temperature decreased to 25° C. The mixture weighed 1150 g and it contained 58.9% furfuryl acetate, i.e., the yield was 100%. The product was washed 3 times with 250 ml water. The furfuryl acetate weighed 686.0 g and its concentration was 93.4%, i.e., the yield was 94.6%.

EXAMPLE 3

Procedure was as in example 2, but acetic anhydride was added to the mixture of furfuryl alcohol and triethyl amine. The crude yield was 1149 g and the concentration was 58.7%, i.e., the yield was 99.5%. The crude product was washed 4 times with 200 ml water, whereby 641.3 g furfuryl acetate was obtained, its concentration was 96.2%, i.e., the yield was 91.0%.

EXAMPLE 4

First 111.2 g (0.600 mole) tributyl amine and then 196.2 g (2.00 mole) distilled furfuryl alcohol were added to 224.6 g (2.20 mole) acetic anhydride. The temperature was allowed to rise to 35° C and was maintained at that for 5 hours. The mixture weighed 528.7 g and its concentration was 52.05%, i.e., the yield was 98.2%. The crude product was washed 3 times with 200 ml water. 5 ml HCl had been added to the second washing water. 264.7 g furfuryl acetate was obtained and its concentration was 95.6%, i.e., the yield was 90.3%.

EXAMPLE 5

The washing waters obtained from the previous example were made alkaline (pH 12.0–12.1) and from the top of the washing waters 99.68 g organic phase was separated which according to the titer contained 96.07 g tributyl amine. In addition, the phases contained some water and furfuryl acetate. Tributyl amine was recovered with a yield of 86.4%.

EXAMPLE 6

The synthesis mixture was prepared as in Example 4, but another wash with 200 ml water was added. Thereafter the procedure was continued as in Example 5. The yield of tributyl amine was 105.9 g, i.e., 95.2%.

EXAMPLE 7

The procedure was as in Example 1 but 5.91 g (0.100 mole) trimethyl amine was used instead of triethyl amine. After the wash the product weighed 138.7 g and contained 96.3% furfuryl acetate, i.e., the yield was 95.3%.

EXAMPLE 8

The procedure was as in Example 2, but 673.8 g (2.5 mole) trihexyl amine was used instead of triethyl amine. Hydrochloric acid was used as an aid in connection with the wash. After the wash the yield was 681.1 g product and it contained 93.2% furfuryl acetate, i.e., the yield was 93.9%.

EXAMPLE 9

The procedure was as in Example 2, but 39.55g (0.5mole) pyridine was used instead of triethyl amine. After the wash the furfuryl acetate weighed 661.1g and its concentration was 96.6% i.e., the yield was 94.3%.

EXAMPLE 10

The procedure was as in Example 1, but 5.61 g (0.05 mole) triethylene diamine (DABCO-Diazabicyclo[2.2.2]octane) was used instead of triethyl amine. The reaction period was 5 h and the temperature 50.0° C. The yield of product after the wash was 140.0 g and it contained 97.0% furfuryl acetate, i.e., the yield was 96.9%.

EXAMPLE 11

The procedure was as in Example 1 but the reaction temperature used after the addition of the raw materials was 80° C, the reaction mixture being heated for 5 hours. 142.2 g product was obtained and its concentration was 91.0%, i.e., the yield was 92.3%.

EXAMPLE 12

The procedure was as in Example 9, but propionic anhydride (715.8 G-5.50 mole) was used instead of acetic anhydride. After the wash the mixture weighed 718.5 g and its concentration was 92.9%, i.e., the yield of furfuryl propionate was 89.5%.

EXAMPLE 13

5.06 g (0.05 mole) triethyl amine and thereafter 143.1 g (1.00 mole) 5-nitro-2furfuryl alcohol were added to 111.2 g (1.10 mole) acetic anhydride. The temperature rose during the addition to 50° C and the mixture was stirred for an additional 5 hours. The mixture was poured into 500 ml water, whereby the produced 5-nitro-2-furfuryl acetate separated as oil. This mixture was stirred at 5° C and inoculating crystals were added, whereby the product crystallized. After the crystallization the product was filtered, washed with water and dried. 180.5 g product with a concentration of 98.8% and with a melting point of 42°–43° C was obtained. The yield was 96.3%.

EXAMPLE 14

37.6 g (0.22mole) chloroacetic anhydride was smelted and thereto was added a mixture which contained 28.6 g (0.20 mole) 5-nitro-2-furfuryl alcohol and 1.58 g (0.020 mole) pyridine. The mixture was heated to 100° C and maintained at that for 5 hours. The mixture was cooled and poured into 100 ml water. Thereby the formed 5-nitro-2-furfuryl chloroacetate crystallized. The product was filtered and washed with water. After drying, 41.9 g (95.4%) product with a melting point of 110°–111° C was obtained.

EXAMPLE 15

The procedure was as in Example 14, but 57.2 g (0.22 mole bromoacetic anhydride and 8.1 g (0.10 mole) N-methyl-pyrrole were used as a catalyst, and a temperature of 80° C was used. After washing and drying 50.1 g (94.8%) 5-nitro-2-furfuryl bromoacetate with a melting point of 99–101° C was obtained.

EXAMPLE 16

The procedure was as in Example 1, but 112.1 g (1.00 mole) 5 methyl-2-furfuryl alcohol was used instead of furfuryl alcohol and the reaction period was 5 hours at 51.0° C. After the wash, 148.0 g 5-methyl-2-furfuryl acetate with a concentration of 97.2% was obtained, i.e., the yield was 93.3%. The quantity of the product obtained by distillation was 138.5 g, with a boiling point of 84–85° C/10 mm Hg.

What is claimed is:

1. A method for producing an ester of a furfuryl alcohol of formula

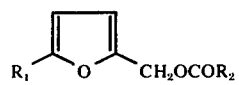

I wherein $R_1$ is hydrogen, a nitro group, a halogen atom or an alkyl group with 1–3 carbon atoms, and $R_2$ is alkyl or alkyl substituted by an halogen atom which comprises reacting a furfuryl alcohol of formula

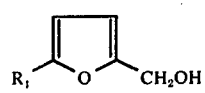

II wherein $R_1$ is as in Formula I, in the absence of a solvent with a lower alkanoic acid anhydride of formula $R_2COOCOR_2$ in which $R_2$ is as defined hereinabove in the proportion of 1 mole of said furfuryl alcohol with 1–1.2 mole of said lower alkanoic acid anhydride and catalysing the reaction with 0.05–0.5 mole of an aliphatic tertiary amine.

2. The method of claim 1, in which the esterification reaction is catalysed with an aliphatic tertiary amine with the formula

wherein $R_3$, $R_4$ and $R_5$ represent an alkyl group with 1–6 carbon atoms.

3. The method according to claim 1, in which the temperature of the esterification reaction is maintained at 0°–100° C.

4. The method according to claim 3 wherein the temperature is 15° – 80° C.

5. The method of claim 1, in which the aliphatic anhydride used is selected from the group comprising acetic anhydride, propionic anhydride, chloroacetic anhydride and bromoacetic anhydride.

6. The method according to claim 1, in which the produced ester of furfuryl alcohol is washed by extracting it with water.

7. The method of claim 1, wherein $R_2$ is an alkyl group substituted with a halogen atom.